United States Patent
Nordmo et al.

(10) Patent No.: US 6,964,569 B2
(45) Date of Patent: Nov. 15, 2005

(54) DENTAL CARE DEVICE

(76) Inventors: Jon Nordmo, Kuholmsveien 80D, N-4632 Kristiansand (NO); Per Høiby, Hans Aanrudsvei 51, N-0956 Oslo (NO)

(*) Notice: Subject to any disclaimer, the term of this patent is extended or adjusted under 35 U.S.C. 154(b) by 56 days.

(21) Appl. No.: 10/343,497
(22) PCT Filed: Aug. 1, 2001
(86) PCT No.: PCT/NO01/00332
§ 371 (c)(1),
(2), (4) Date: Jan. 31, 2003
(87) PCT Pub. No.: WO02/13721
PCT Pub. Date: Feb. 21, 2002

(65) Prior Publication Data
US 2004/0014001 A1 Jan. 22, 2004

(30) Foreign Application Priority Data
Aug. 8, 2000 (NO) .......................... 20003993
Apr. 9, 2001 (NO) .......................... 20011794

(51) Int. Cl.⁷ .............................. A61C 3/02
(52) U.S. Cl. ....................................... 433/88
(58) Field of Search .................. 433/88; 451/90, 451/102; 606/131

(56) References Cited

U.S. PATENT DOCUMENTS

| | | | | |
|---|---|---|---|---|
| 4,151,648 A | * | 5/1979 | Hirth ........................... | 433/78 |
| 4,941,298 A | * | 7/1990 | Fernwood et al. ............. | 451/90 |
| 5,120,219 A | * | 6/1992 | De Farcy ...................... | 433/88 |
| 5,344,317 A | * | 9/1994 | Pacher et al. .................. | 433/85 |
| 5,934,904 A | * | 8/1999 | Elrod et al. ................... | 433/88 |
| 6,106,288 A | * | 8/2000 | Brassil et al. ................. | 433/88 |
| 2002/0123020 A1 | * | 9/2002 | Aumuller et al. ............. | 433/88 |

FOREIGN PATENT DOCUMENTS

WO    WO 94/08533 A1    4/1994

* cited by examiner

Primary Examiner—Cary E. O'Connor
(74) Attorney, Agent, or Firm—Rodman & Rodman

(57) ABSTRACT

A pneumatic dental care device for private use which by means of a combination of air, liquid and powder at high pressure cleans the user's teeth and removes plaque and discoloration. The device consists of a base unit (100) and a hand unit (300) which are connected via a flexible, sheathed tube and wire bundle (200). The base unit contains a microcompressor (120), a liquid container (130) and a powder container (140). Liquid and/or powder are discharged at high pressure through an exchangeable nozzle unit (400) on the hand unit. The nozzle unit consists of one or more flexible (bendable) jet stems (401). The microprocessor, the powder container and the liquid container can be replaced by an exchangeable compressed air tank and/or pressurized liquid and/or powder containers in different configurations. The components of the device can also be integrated into a hand-held unit.

13 Claims, 5 Drawing Sheets

DENTAL CARE DEVICE

The present invention relates to devices for personal care and hygiene, more specifically a pneumatic dental care device for private use which by means of a combination of air, liquid and powder at high pressure cleans the user's teeth.

Various mechanical dental care devices are known. For private household use there are a number of variants of rotating brushes. However, a common feature of these devices is that they are not particularly suitable for removing dental plaque and discoloration on the teeth. Moreover, it can be difficult to clean effectively between the teeth with such brushes.

Other known mechanical dental care devices for private use include an apparatus that is described in U.S. Pat. No. 4,214,871 ("Method and apparatus for cleaning teeth and removing plaque", Carter H. Arnold, 29.07.80). The apparatus is connected to a water tap and is driven by the water pressure. Powder in a container is mixed with water, whereupon the mixture is discharged from a nozzle.

Another known mechanical dental care apparatus for private use is described in DE-C3-2653494 ("Gerät zur K operpflege", Les Produits Associés LPA S.A., 18.07.85). The apparatus comprises a liquid tank and a container for dry material. The dry material is mixed with the liquid on use.

Furthermore, WO 94/08533 ("Dispositif de pulvérisation destiné au nettoyage des dents") describes a unit for personal dental care. Here, a compressor is used to pressurise one or more containers containing water or another liquid for dental treatment, so that the liquid(s) are discharged through a nozzle. The liquid from the various containers is carried together in one tube to a chamber in the hand unit where it is atomised by means of air for onward feeding to a nozzle. The characteristic feature of this device is the actual liquid atomising process, i.e., the formation of "liquid particles" in the chamber by direct supply of air from the compressor. An atomisation chamber of this kind is not intended for or suitable for use of powder, and the chamber is ill-suited for mixing powder with a liquid. Attempts to mix powder and liquid would result in the chamber and its nozzle outlet tube becoming blocked very quickly. At the very least the chamber, connected tubes and the nozzle would have to be cleaned thoroughly after each use by removing solidified liquid and powder paste. To all appearances, the invention according to WO 94/08533 would not function if one of the containers is filled with powder. The different properties of the two media (liquid, powder) would lead to complications upon the initial mixing of the media and their onward movement in the tube (WO 94/08533, FIG. 2, reference numeral 12), in addition to the aforementioned problems of blockage in the atomisation chamber.

For professional use in dental clinics, there are pneumatic dental care devices where liquid and powder are used in combination. These have a separate air compressor and are connected directly to the water mains. The devices are not mobile and require extensive installation work that must be done by a professional installation contractor. Furthermore, the known professional pneumatic devices have only one nozzle. Examples of such professional units are described in EP 00 97288 A2 ("A dental prophylactic apparatus") and FR 2 599 244 ("Appareil de nettoyage des dents par projection").

There is therefore a greatly felt need for a pneumatic dental care device for private use which by means of a combination of air, liquid and powder at high pressure cleans the user's teeth.

According to the invention, there is thus provided a pneumatic dental care device for private use that is characterised by the characteristic features.

The inventive device is a tooth-cleaning appliance that can be used in the home to enhance and improve the efficiency of dental cleaning and oral hygiene to a far greater extent than the known devices within the same area of usage. The device is a household appliance which by means of high pressure and the use of the powder in part mechanically removes discoloration, plaque and tartar. This is distinct from the aforementioned document WO 94/08533 which only comprises a spraying or rinsing with a liquid and is therefore not considered to produce as good a treatment effect as the device according to the invention.

"High pressure spraying" of teeth is more efficient than all other known methods of cleaning teeth, especially if it includes a combination of pressurised powder and liquid.

The device is novel in that it gives a private user the possibility of cleaning his teeth himself at home in a way that only a dentist can do today, thus enabling him to reduce the number of visits he makes to the dentist. Each dental visit will be less comprehensive, faster and thus cheaper. Regular use of the device means that it is possible to maintain clean, white and healthy teeth also in the period between dental visits.

The device results in a time-saving and effective cleaning of the teeth as there is no need to combine the use of a toothbrush with, for example, dental floss and/or tooth picks. Furthermore, the inventive device removes dental plaque, discoloration, tartar, food debris and the like more efficiently per time unit than the known mechanical tooth cleaning devices for home use, including traditional electric toothbrushes. The device according to the invention cleans gingival pockets, which is especially useful for users who have gum disease. The device gives a substantially enhanced result as regards oral hygiene (measured by the plaque index score) and gives a better visual result. The device constitutes a total solution for fluorine and toothpaste (prevents caries and periodontitis), and can in daily use replace the toothbrush, dental floss and tooth picks.

The position and design of the nozzle or nozzles permits a cleaning of several tooth surfaces at once, as the nozzles are directed towards several sides and clean the whole tooth, and also between teeth. There will be no risk of a build-up of bacteria in the device, which is a current problem with all known brush types, both manual and electric. Therefore the device can be used by several household members.

A comparison between the device according to the invention and other teeth-cleaning methods performed at home can be summarised as follows:

| | Removal of plaque | Area of tooth surface treated | Effect on aesthetic result | Cleaning of gums |
| --- | --- | --- | --- | --- |
| Toothbrush with ordinary toothpaste | Dependent on cleaning time | ca. 60% | Minimal | Limited |
| Electric toothbrush | To a certain degree | ca. 70% | Some | Limited |
| Device according to the invention | Completely | ca. 90%–95% | Great | Yes |

It should be appreciated that the attached drawings show only a basic exemplary embodiment, and that this should not be understood as defining the limits of the invention. In the drawings the relevant parts are indicated by reference numerals that will also be used in the following description.

Figure 1:
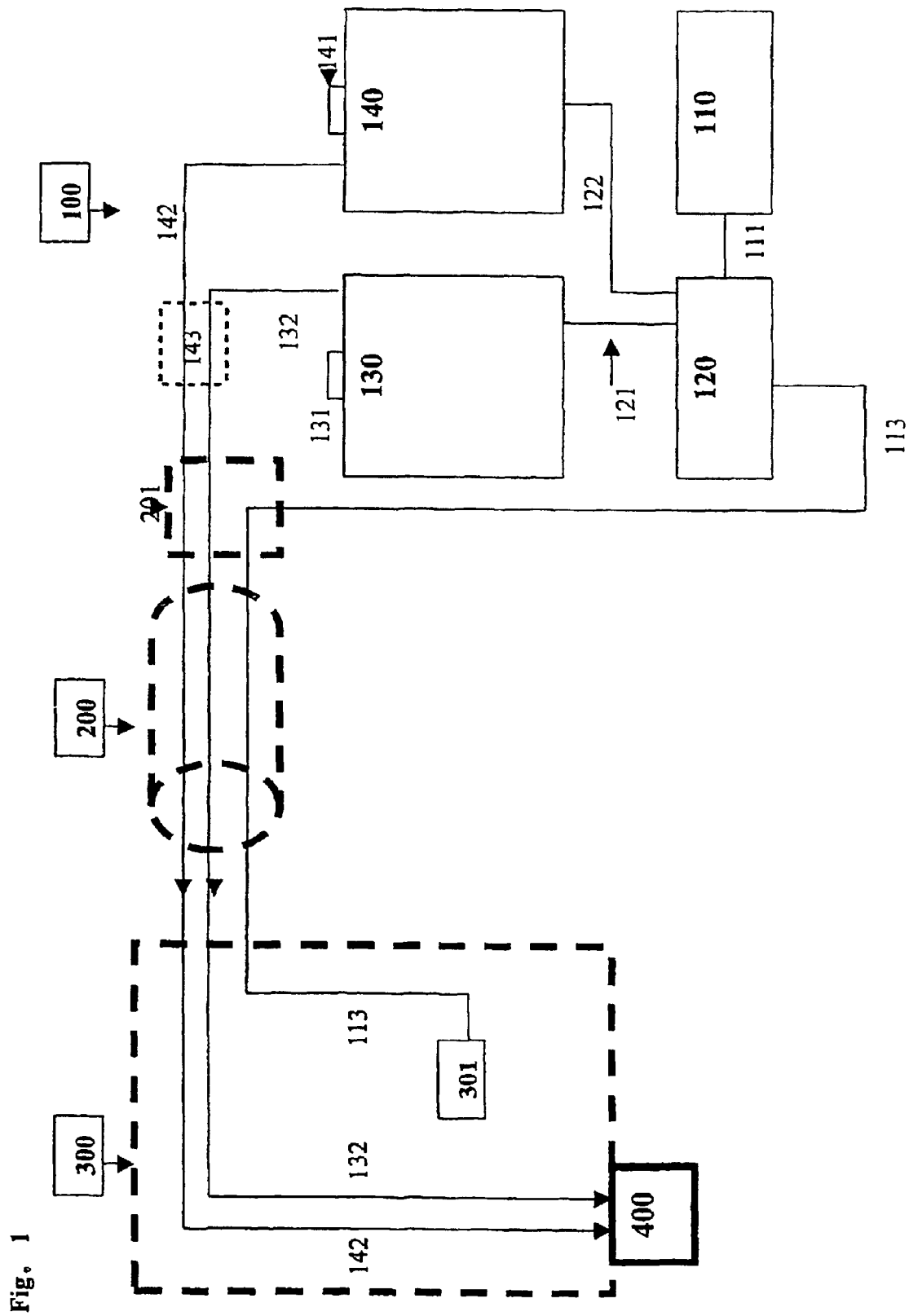
FIG. 1 is a schematic diagram of the device according to the invention.

The device is a pneumatic dental care device for home use which by means of a combination of air, liquid and powder cleans the user's teeth and removes dental plaque and discoloration. The device consists of two main parts: a base unit 100 and a hand unit 300. The base unit and the hand unit are connected via a flexible, sheathed tube and wire bundle 200. The base unit contains a power source 110 which via a power supply line 111 supplies power to a microcompressor 120. Via the tubes 121 and 122, the microcompressor 120 pressurises a liquid container 130 and a powder container 140 respectively. The containers 130 and 140 include respective caps 131 and 141. The containers 130 and 140 have visual volume indicators (not shown). The compressed air carries liquid and powder at high pressure (adjustable, preferably between 4.5 bar and 7.5 bar) through suitable tubes 132 and 142, via the tube and wire bundle 200, through the hand unit 300 and into an attached, exchangeable nozzle unit 400. The flow through the tubes 132, 142 and thus the mixture ratio of liquid to powder as the media exit the nozzle orifice is selectively adjustable by means of a mixer unit 143 mounted inside the base unit 100.

Figure 2:
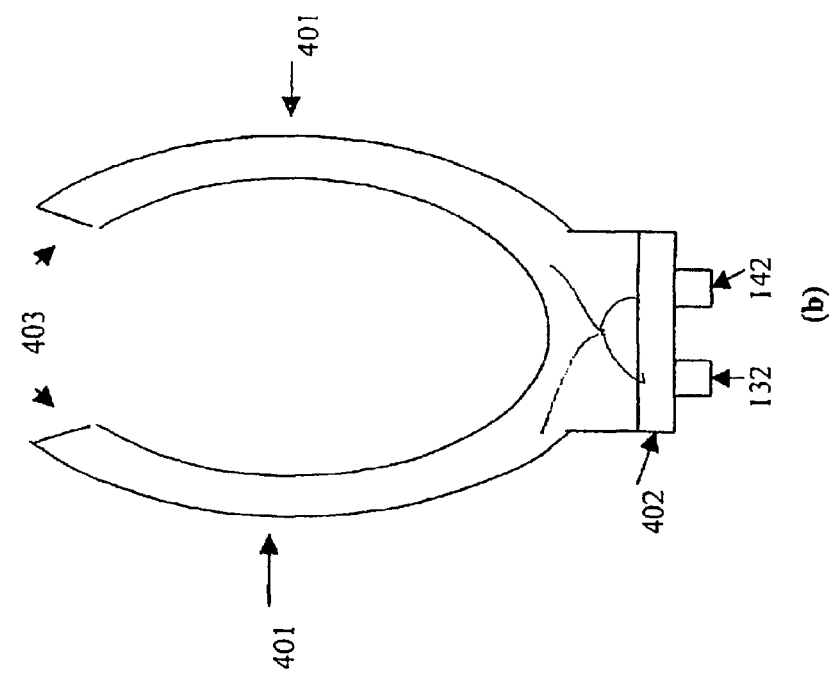
FIG. 2 is a side view of two different alternative nozzles.
Figure 2:
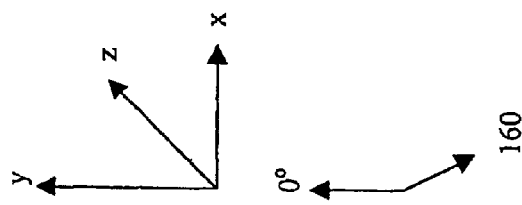
Figure 2:
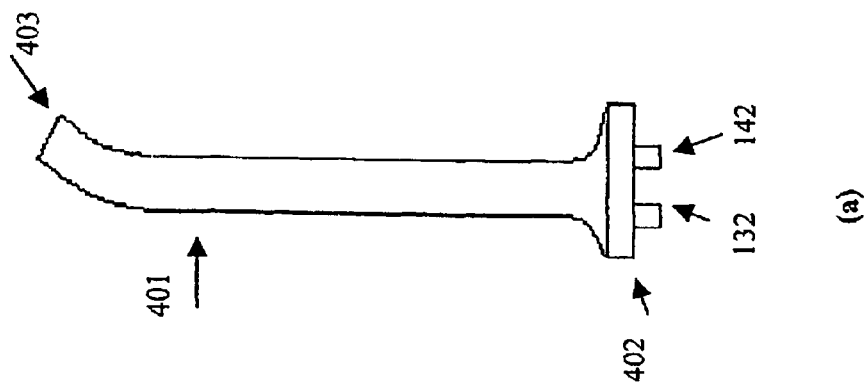
Figure 3:
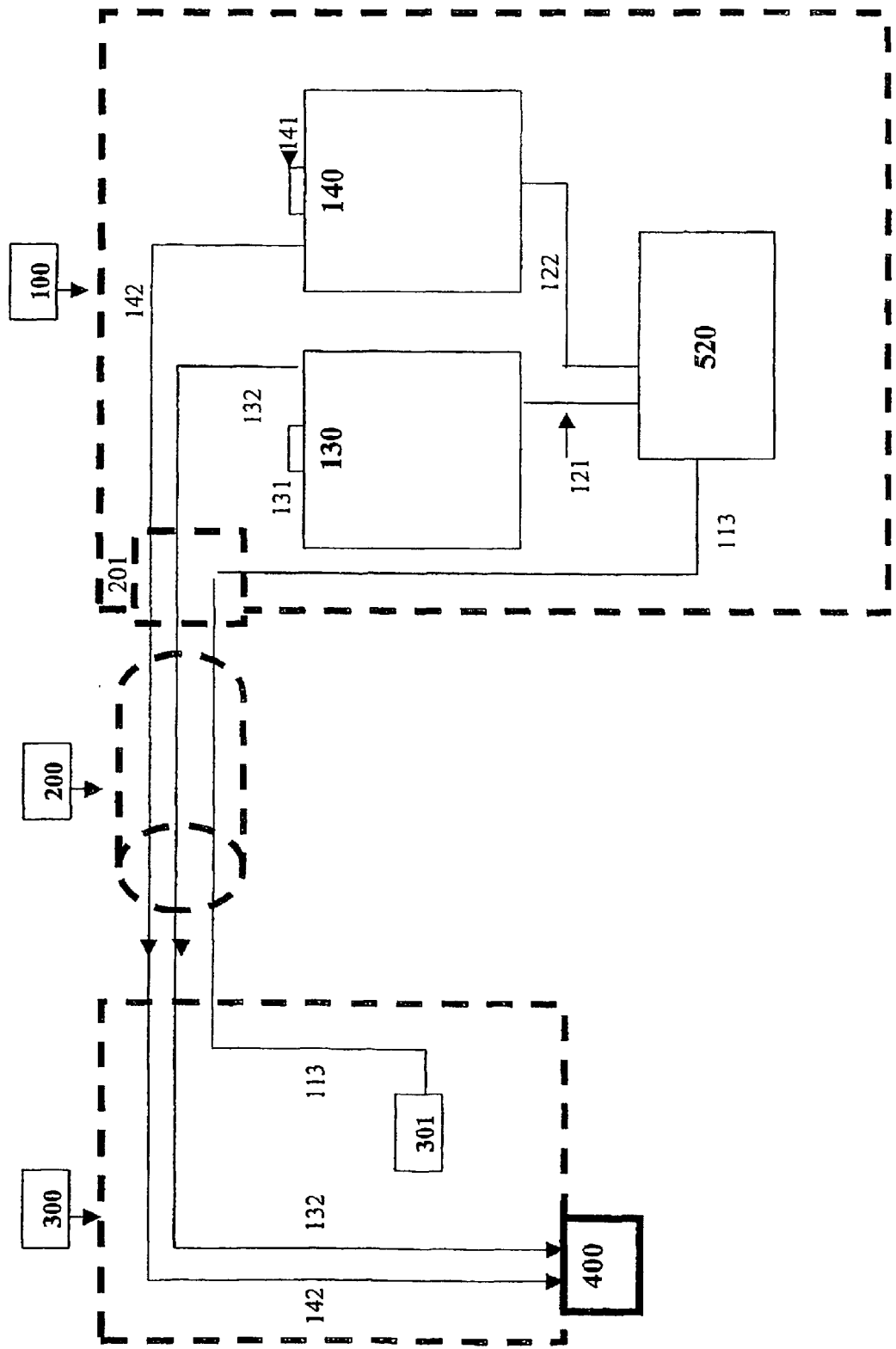
FIG. 3 is a schematic diagram of the device according to the invention, wherein the microcompressor has been replaced by an exchangeable compressed air tank.
Figure 4:
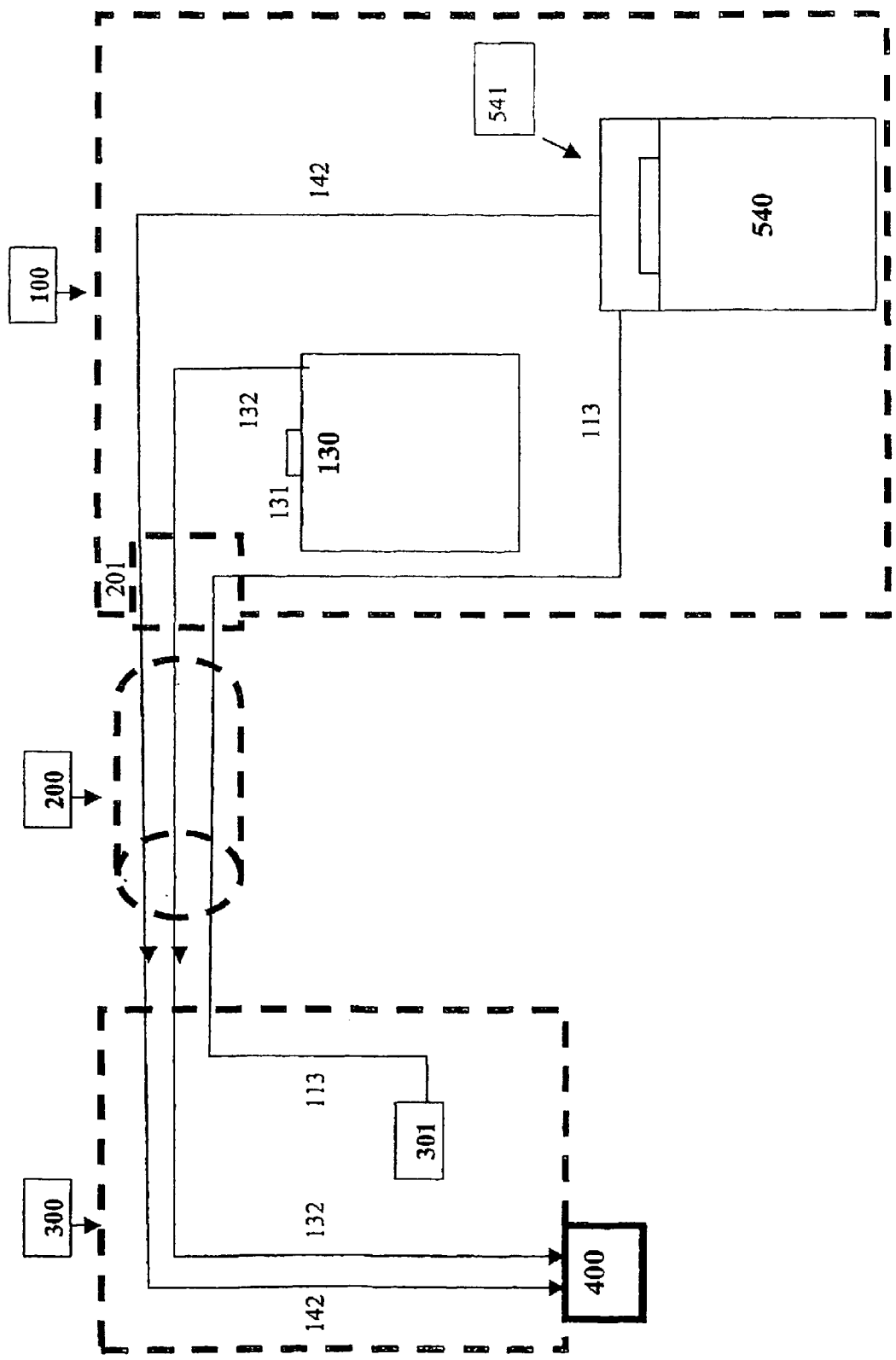
FIG. 4 is a schematic diagram of the device according to the invention, wherein the microcompressor and the powder container have been replaced by an exchangeable pressurised powder container with associated coupling cap and valve.
Figure 5:
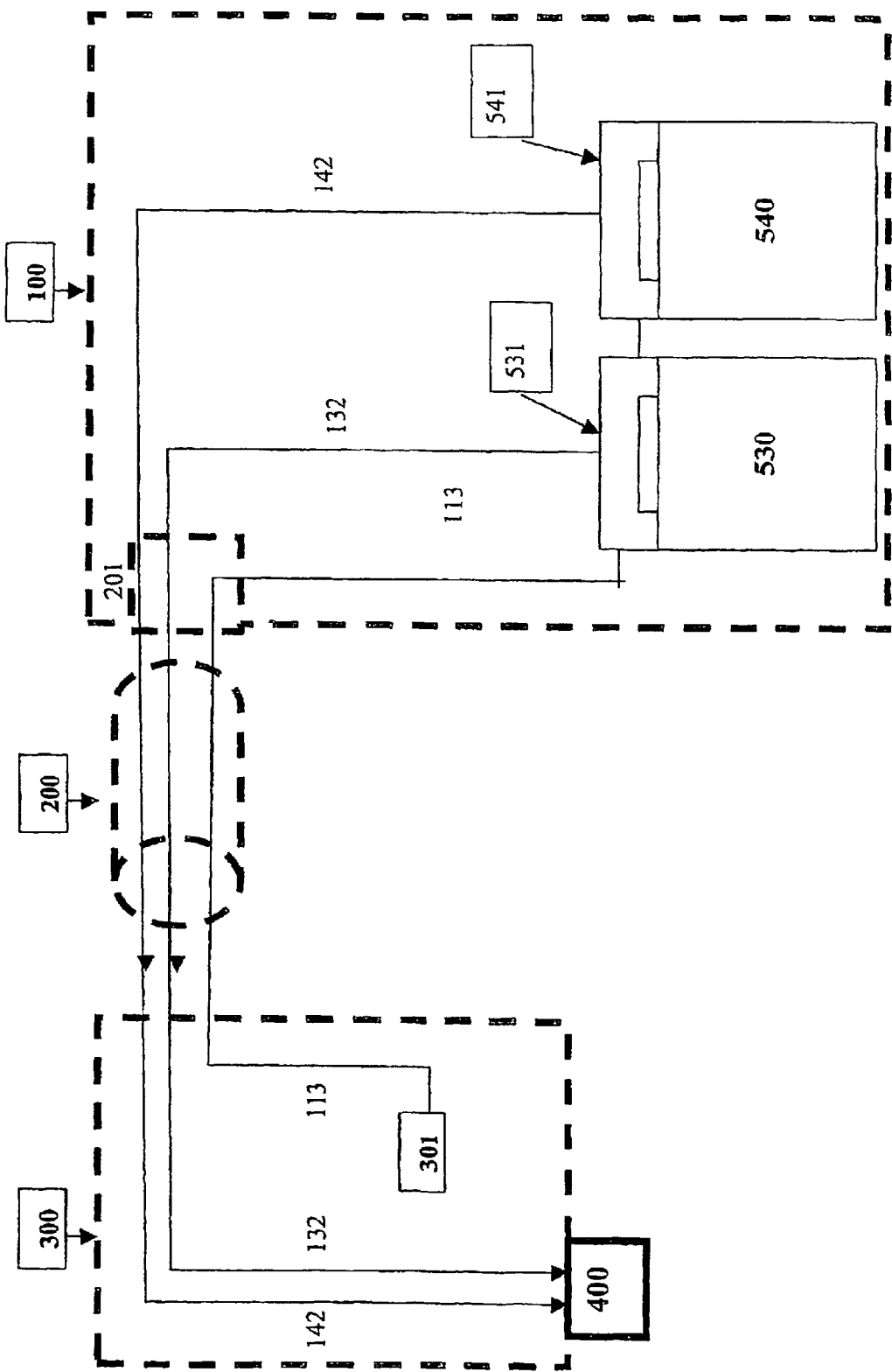
FIG. 5 is a schematic diagram of the device according to the invention, wherein the microcompressor, the powder container and the liquid container have been replaced by an exchangeable pressurised powder container with associated coupling cap and valve and an exchangeable pressurised liquid container with associated coupling cap and valve.

The term "mixer unit" should be understood to mean a unit 143 that adjusts the flow ratio between the media in their respective tubes 132, 142. The media (e.g., liquid and powder) are not mixed in the device at all, but are passed out through the nozzle in separate tubes, in a way that is known per se, as shown in, e.g., FIGS. 1 and 2. If so desired, the mixer unit can be adjusted so that only one of the media exits the nozzle.

The microcompressor 120 is connected to a control unit 301 via the line 113 to enable the microcompressor 120 to be switched on, controlled and switched off by means of the control unit 301 mounted in the hand unit 300. The tube and wire bundle 200 are coiled up on a reel device 201 in the base unit when the hand unit is not in use. The hand unit 300 is ergonomically designed to be suitable for use for personal dental care.

The nozzle unit 400 consists of a base 402 that is releasably attached to the outer end of the hand unit 300. The nozzle unit receives media under pressure (e.g., liquid, powder) is in the respective tubes 132, 142. The actual nozzle principle is known, the ducts inside the nozzle being so arranged that the media are discharged from the nozzle orifice or orifices 403 in coaxial relation. This means to say that one of the media (usually the powder) is passed out in a jet, whilst the other medium (usually the liquid) is passed out as an annular "tube" coaxial with the jet. Thus, the media are not mixed until they meet the desired point in the user's mouth. The powder thus acts as an abrasive agent and carries out a mechanical cleaning per se, whilst the initial function of the liquid is to cushion or protect. Subsequently, the liquid will function as a rinsing agent for the particles on and near the teeth, and provide a treatment of the teeth if the liquid has a dental care agent added thereto. The adjustable high pressure and the design of the nozzle permit a particle formation of the liquid as it leaves the nozzle orifice. An aerosol of this kind, or "water particles", will be capable of being spread in an effective way and able to gain access in order to administer care to places in the user's mouth that could not have been reached by, e.g., a water jet.

The nozzle unit may consist of one or more jet stems 401, where each jet stem is flexible so that it can be adjusted (bent) by the user into angular positions between 0° and 180° (preferably between 0° and 160°) relative to the y axis of the nozzle unit. Each jet stem 401 is fixed to the nozzle base 402 at the same angle relative to each other in the xz plane.

In an alternative embodiment of the invention, the microcompressor 120 is replaced by an exchangeable compressed air tank 520. In yet another alternative embodiment of the invention, the microcompressor 120 and the powder container 140 are replaced by an exchangeable pressurised powder container 540 with associated coupling cap and valve 541.

In another alternative embodiment of the invention, the microcompressor 120, the powder container 140 and the liquid container 130 are replaced by an exchangeable pressurised powder container 540 with associated coupling cap and valve 541 and an exchangeable pressurised liquid container 530 with associated coupling cap and valve 531.

In yet another alternative embodiment of the invention, the base unit 100, the tube and wire bundle 200 and the hand unit 300 are integrated in a hand-held unit. The use of exchangeable pressurised containers means that the integrated unit can be given a convenient and useful size.

What is claimed is:

1. A pneumatic dental care device for private use which by means of a combination of air, liquid and powder cleans the user's teeth and removes plaque and discoloration, consisting of a base unit connected via a flexible sheathed tube and wire bundle to a hand unit, where the base unit contains a power source which, via a power supply lead, supplies power to a microcompressor, characterised in that:

the microcompressor has first and second pressurizing tubes that respectively pressurize a liquid container and a powder container;

a tube for transferring liquid is connected via a tube and wire bundle to the liquid container and a hand unit having an attached exchangeable nozzle unit in order at a positive pressure to be able to pass a liquid medium therefrom via the tube and wire bundle through the hand unit and into the attached, exchangeable nozzle unit;

a tube for transferring powder is connected via the tube and wire bundle to the powder container and the hand unit in order at a positive pressure to be able to pass a powder medium therefrom via the tube and wire bundle through the hand unit and into the attached exchangeable nozzle unit;

the flow through the respective tubes for transferring liquid and powder is selectively adjustable by means of a mixing unit mounted in a base unit, in order thus to adjust the ratio of liquid flow to powder flow; and wherein the base unit, the tube and wire bundle and the hand unit are integrated in a hand-held unit.

2. A device according to claim 1, characterised in that the microcompressor is selectively controllable in order on use to generate a positive pressure, between 4.5 and 7.5 bar.

3. A device according to claim 1, characterised in that powder is discharged from the nozzle in powder form.

4. A device according to claim 1, characterised in that liquid is discharged from the nozzle in an atomised state.

5. A device according to claim 1, characterised in that liquid is discharged from the nozzle in a tubular (annular) jet, generally in coaxial relation with said powder.

6. A device according to claim 1, characterised in that the microcompressor is switched on, controlled and switched off by means of a control unit mounted in the hand unit.

7. A device according to claim 1, characterised in that the tube and wire bundle is coiled up on a reel device when the hand unit is returned to the base unit after use.

8. A device according to claim 1, characterised in that the hand unit is ergonomically designed to be suitable for use for personal dental care.

9. A pneumatic dental care device for private use which by means of a combination of air, liquid and powder cleans the user's teeth and removes plaque and discoloration, consisting of a base unit connected via a flexible sheathed tribe bundle to a hand unit, where the base unit contains a compressed air tank, characterised in that:

the compressed air tank has first and second pressurizing tubes that respectively pressurize a liquid container and a powder container;

a tube for transferring liquid is connected via a tube bundle to the liquid container and a hand unit having an attached exchangeable nozzle unit in order at a positive pressure to be able to pass a liquid medium therefrom via the tube bundle through the hand unit and into the attached, exchangeable nozzle unit;

a tube for transferring powder is connected via the tube bundle to the powder container and the hand unit in order at a positive is pressure to be able to pass a powder medium therefrom via the tube bundle through the hand unit and into an attached nozzle unit;

the flow through the respective tubes for transferring liquid and powder is selectively adjustable by means of a mixing unit mounted in a base unit, in order thus to adjust the ratio of liquid flow to powder flow; and wherein the base unit, the tube bundle and the hand unit are integrated in a hand-held unit.

10. A pneumatic dental care device for private use which by means of a combination of air, liquid and powder cleans the user's teeth and removes plaque and discoloration, consisting of a base unit connected via a flexible sheathed tube and wire bundle to a hand unit, where the base unit contains a power source which, via a power supply lead, supplies power to a microcompressor, characterised in that:

the microcompressor has a first pressurizing tube that pressurizes a liquid container;

a tube for transferring liquid is connected via a tube and wire bundle to the liquid container and a hand unit having an attached exchangeable nozzle unit in order at a positive pressure to be able to pass a liquid medium therefrom via the tube and wire bundle through the hand unit and into the attached, exchangeable nozzle unit;

the base unit includes an exchangeable pressurized powder container with associated coupling cap and valve and has a tube for transferring powder connected via the tube and wire bundle to the powder container and the hand unit in order at a positive pressure to be able to pass a powder medium therefrom via the tube and wire bundle through the hand unit and into the attached, exchangeable nozzle unit;

the flow through the respective tubes for transferring liquid and powder is selectively adjustable by means of a mixing unit mounted in a base unit, in order thus to adjust the ratio of liquid flow to powder flow; and wherein the base unit, the tube and wire bundle and the hand unit are integrated in a hand-held unit.

11. A device according to claim 10, characterised in that the said integrated hand-held unit is operated by exchangeable pressurised containers.

12. A device according to claim 10, characterised in that the said integrated hand-held unit is operated by a microcompressor.

13. A pneumatic dental care device for private use which by means of a combination of air, liquid and powder cleans the user's teeth and removes plaque and discoloration, consisting of a base unit connected via a flexible sheathed tube bundle to a hand unit characterized in that, the base unit contains an exchangeable pressurised liquid container with associated coupling cap and valve and an exchangeable pressurised powder container with associated coupling cap and valve;

a tube for transferring liquid is connected via a tube bundle to the pressurized liquid container and a hand unit having an attached exchangeable nozzle unit in order at a positive pressure to be able to pass a liquid medium therefrom via the tube bundle through the hand unit and into the attached, exchangeable nozzle unit;

a tube for transferring powder is connected via the tube bundle to the pressurized powder container and the hand unit in order at a positive pressure to be able to pass a powder medium therefrom via the tube bundle through the hand unit and into the attached, exchangeable nozzle unit;

the flow through the respective tubes for transferring liquid and powder is selectively adjustable by means of a mixing unit mounted in the base unit, in order thus to adjust the ratio of liquid flow to powder flow; and wherein the base unit, the tube bundle and the hand unit are integrated in a hand-held unit.

* * * * *